US009802970B2

(12) United States Patent
Yao et al.

(10) Patent No.: US 9,802,970 B2
(45) Date of Patent: Oct. 31, 2017

(54) PROCESS FOR PREPARING DIALKYLPHOSPHINATE AND A PRODUCT THEREOF

(71) Applicants: NINGBO INST. OF MATERIALS TECH. & ENG., CHINESE ACAD. OF SCIENCES, Ningbo (CN); PRESAFER (QINGYUAN) PHOSPHOR CHEMICAL COMPANY LIMITED, Qingyuan, Guangdong (CN)

(72) Inventors: Qiang Yao, Ningbo (CN); Yueying Zhao, Ningbo (CN); Tianbo Tang, Ningbo (CN); Kan Zhou, Qingyuan (CN)

(73) Assignees: NINGBO INST. OF MATERIALS TECH. & ENG., CHINESE ACAD. OF SCIENCES, Ningbo (CN); PRESAFER (QINGYUAN) PHOSPHOR CHEMICAL COMPANY LIMITED, Qingyuan (CN)

( * ) Notice: Subject to any disclaimer, the term of this patent is extended or adjusted under 35 U.S.C. 154(b) by 0 days.

(21) Appl. No.: 15/122,345

(22) PCT Filed: Apr. 1, 2014

(86) PCT No.: PCT/CN2014/074507
§ 371 (c)(1),
(2) Date: Aug. 29, 2016

(87) PCT Pub. No.: WO2015/149265
PCT Pub. Date: Oct. 8, 2015

(65) Prior Publication Data
US 2016/0368936 A1 Dec. 22, 2016

(51) Int. Cl.
*C07F 9/30* (2006.01)
*C07F 9/48* (2006.01)
(Continued)

(52) U.S. Cl.
CPC ............ *C07F 9/301* (2013.01); *C07F 9/3211* (2013.01); *C07F 9/4816* (2013.01); *C08K 5/5313* (2013.01); *C09K 21/12* (2013.01)

(58) Field of Classification Search
None
See application file for complete search history.

(56) References Cited

U.S. PATENT DOCUMENTS 3,322,716 A * 5/1967 Klein .................. C07F 9/30 521/85
5,773,556 A * 6/1998 Kleiner ................ C08K 5/5313 524/126

(Continued)

FOREIGN PATENT DOCUMENTS

CN 101891762 A 11/2010
CN 103172670 A 6/2013
(Continued)

OTHER PUBLICATIONS

International Search Report issued in PCT/CN2014/074507 dated Dec. 30, 2014 (2 pages).

*Primary Examiner* — Yate K Cutliff
(74) *Attorney, Agent, or Firm* — Osha Liang LLP

(57) ABSTRACT

The present provides a process for preparing dialkyl phosphinate, comprising: (1) firstly adding 0-99% of the total weight of phosphinic acids and/or salts thereof and a solvent into a reaction kettle; (2) in the reaction kettle in the presence of alkene and initiator, continuously adding 1-100% of the total weight of the phosphinic acids and/or salts thereof into the reaction system, during the addition process, when the mole contents of monoalkyl phosphinic (Continued)

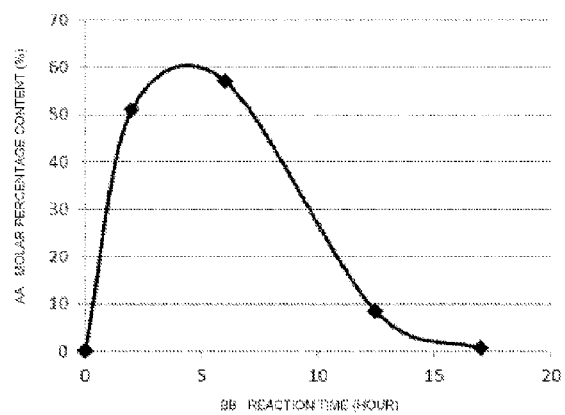

acids and/or salts thereof account for 10% or less of the total molar contents of phosphorus in the reaction system, stopping adding the phosphinic acids and/or salts thereof. Also providing a dialkyl phosphinate flame retardant prepared by above preparation process.

19 Claims, 1 Drawing Sheet

(51) Int. Cl.
*C07F 9/32* (2006.01)
*C08K 5/5313* (2006.01)
*C09K 21/12* (2006.01)

(56) References Cited

U.S. PATENT DOCUMENTS

| | | | |
|---|---|---|---|
| 5,973,194 A * | 10/1999 | Weferling | C07F 9/30 252/609 |
| 6,300,516 B1 | 10/2001 | Weferling et al. | |
| 6,355,832 B1 * | 3/2002 | Weferling | C07F 9/30 562/8 |
| 6,534,673 B1 * | 3/2003 | Weferling | C07F 9/30 562/8 |
| 7,635,785 B2 | 12/2009 | Bauer et al. | |

FOREIGN PATENT DOCUMENTS

| | | |
|---|---|---|
| CN | 103319524 A | 9/2013 |
| CN | 104119377 A | 10/2014 |

* cited by examiner

FIG. 9B

PROCESS FOR PREPARING DIALKYLPHOSPHINATE AND A PRODUCT THEREOF

TECHNICAL FIELD

The present invention belongs to the technical field for preparing flame retardants, in particular relates to a process for preparing dialkylphosphinate and a product thereof.

BACKGROUND

Aluminum dialkylphosphinate and zinc dialkylphosphinate are halogen-free flame retardants with good thermal stability and flame resistance, and now have been widely used to prevent polyamides and polyesters from flaming as an alternative to brominated flame retardants. They can be prepared by various methods.

U.S. Pat. Nos. 6,300,516 and 6,355,832 describe a method for preparing aluminum dialkylphosphinate by feeding phosphinic acid or alkali metal salts thereof into a kettle at one time and reacting the phosphinic acid or alkali metal salts thereof with alkenes in the presence of azo initiators to prepare the intermediate dialkyl phosphinic acids or alkali metal salts thereof, the products obtained were then mixed with aluminum salt to produce aluminum dialkylphosphinate. The intermediate dialkylphosphinic acids/alkali metal salts thereof prepared by the method above contain a large amount of the long chain alkyl phosphinates/alkali metal salts, wherein the contents of which are between 7% and 12%. Physical properties of the engineering plastics will be affected as a result of containing too much long chain alkyl phosphinate, and the the product quality control will be affected if the contents of the long chain alkyl phosphinic acids/alkali metal salts vary in a large range. Therefore, it is necessary to control the contents of the long chain alkyl phosphinate to be less than 10% and to keep it stable.

U.S. Pat. No. 7,635,785 describes a method for preparing dialkylphosphinate by, using water as the co-solvent, feeding phosphinate into a kettle at one time and reacting phosphinate with alkene in the presence of an initiator to prepare dialkylphosphinate. The method described above can effectively control the contents of the long chain alkyl phosphinate to be less than 6%. However, due to the solubility of ethylene in water is very low, a high pressure has to be used in this method (20 bar) in order to achieve a satisfactory yield. The use of high pressure condition increases the risk of the reaction, therefore this method is not suitable for industrial production.

Chinese Patent CN101891762 describes a method for preparing sodium diethylphosphinate by adding sodium phosphinate into a kettle at one time and reacting the sodium phosphinate with ethylene in the presence of photoinitiators to produce sodium diethylphosphinate. Since the sodium diethylphosphinate prepared by the method above contains 2.5% mole or more of sodium monoethylphosphinate, aluminum diethylphosphinate transformed from the sodium diethylphosphinate is inevitably doped with a high level of aluminum monoethylphosphinate which has lower thermal stability, thereby limiting the application of the products in factory plastics.

Chinese Patent CN103319524 describes a method for preparing dialkylphosphinate by feeding sodium phosphinate into a kettle at one time and reacting the sodium phosphinate with alkene in the presence of metal complexes and initiators to produce dialkylphosphinate. Although the method above avoids the production of monoalkyl phosphinate, a variety of organic solvents are used in order to stabilize the transition metal complexes, which adversely affects the purification of the product and the environment.

Chinese Patent CN103172670 describes a method for directly preparing aluminum diethylphosphinate by, using water as solvent, feeding aluminum phosphinate into the kettle at one time and reacting the aluminum phosphinate with ethylene in the presence of initiators to produce aluminum diethylphosphinate directly. Because the method above requires reactions at high pressure, there are safety risks, which is not suitable for industrial production.

So far, all methods which have been reported for preparing dialkyl phosphinic acid or salts thereof involve feeding phosphinic acid/salts thereof into a reaction kettle at one time. All these methods need to be improved, as all of them have drawbacks in controlling the contents of long chain alkyl phosphinates and monoalkyl phosphinates.

DISCLOSURE OF THE INVENTION

Technical Problem

In order to overcome the drawbacks and shortcomings of the prior art, one object of the present invention is to provide a process for preparing dialkylphosphinate which can simply control the contents of long chain alkyl phosphinic acids/salts thereof and monoalkyl phosphinic acids/salts thereof and significantly shorten the reaction time.

The present invention further provides a diethylphosphinate flame retardant.

Solution of the Problem

A process for preparing dialkylphosphinate, comprising the following steps:

(1) firstly adding 0-99% of the total weight of phosphinic acid and/or salts thereof, and a solvent into a reaction kettle;

(2) in the reaction kettle in the presence of alkene and initiator, continuously adding 1-100% of the total weight of the phosphinic acid and/or salts thereof into the reaction system, during the addition, when the total mole fractions of monoalkyl phosphinic acids and/or salts thereof in their declining curves account for 10% or less of the total moles of phosphorus in the reaction system, stopping adding additional phosphinic acid and/or salts thereof, thereby obtaining dialkylphosphinic acids and/or salts thereof.

Wherein, the phosphinate is one or more of the phosphinic acid salts of Li, Na, K, Mg, Ca, Ba, Fe, Zr, Al, Sn, Sr, Sb, Ge, Ti and Zn. And the salts of Li, Na and K are more preferable.

The initiator is one or more of azo initiators, peroxide initiators and photoinitiators. The amount of the initiator added may be determined as required, and generally the moles of the initiator added is 0.1-5% of the total moles of phosphinic acid and/or salts thereof, more preferably 0.3-4%.

The azo initiator is a cationic and/or non-cationic azo initiator.

Preferably, the initiator is one or more of azobis(isobutyronitrile), 4,4'-azobis(4-cyano pentanoic acid), 2,2'-azobis(2-methyl butyronitrile), 2,2'-azobis(2-amidino propane) dihydrochloride and 2,2'-azodiisobutyl amidinedihydrochloride.

The peroxide initiator is preferably an inorganic peroxide and an organic peroxide free radical initiator, and particularly preferably is one or more of hydrogen peroxide, ammonium persulfate, potassium persulfate, sodium persulfate, sodium percarbonate, benzoyl peroxide, di-tert-butyl peroxide, t-butyl perbenzoate and peracetic acid.

The alkene has the following structure:

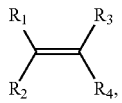

wherein $R_1$-$R_4$ may be the same or different, and are hydrogen, $C_{1-18}$ alkyl or cycloalkyl, phenyl, benzyl, alkyl-substituted phenyl group, or alkoxy ketone group.

Preferably, the alkene is a α-alkene having linear or branched chains, preferably the α-alkene is ethylene, propylene, isopropylene, butylene, isobutylene, pentene, isopentene, hexene, isohexene, octene, isooctene, docosene, isodocosene and mixtures of 2,4,4-trimethyl-pentene isomers.

The cyclic alkene having the following structure, in particular cyclopentene, cyclohexene or cyclooctene are also applicable.

The reaction is preferably carried out in a solvent. The solvent is preferably an organic carboxylic acid, water, or their mixture.

The reaction is preferably carried out at a temperature of 20-180° C., particularly preferably at a reaction temperature of 60-150° C., and more particularly preferably at a reaction temperature of 80-130° C.

The reaction is preferably carried out at 0.1-5 MPa. For the alkene which is gas under atmosphere pressure, the pressure is preferably 0.1-3 MPa, particularly preferably 0.2-1 MPa, and more particularly preferably 0.3-0.6 MPa.

In order to improve the solubilities of the alkenes and increase the reaction rate, it is preferably that the activated carbon or charcoal is simultaneously added when adding the phosphinic acid and/or salts thereof. The amount of charcoal or activated carbon used is between 0.01% and 5% of the total weight of the solution. It is difficult to filtrate the charcoal if the amount of charcoal is too high, however the reaction rate cannot be increased significantly if the amount of charcoal is too low.

In the present invention, the phosphinic acid and/or salts thereof can be continuously added into the reaction kettle at the beginning of the reaction, or after a period of time the reaction has been carried out. Preferably, the phosphinic acid and/or salts thereof are added in such a manner: firstly 1-99% of the total weight is added in step (1), and 1-99% of the total weight is added in step (2); and further preferably, firstly 60-85% of the total weight is added in step (1), and 15-40% of the total weight is added in step (2).

The additionally added phosphinic acid and/or salts thereof can be in the form of solid or solution, preferably in the form of a solution of phosphinic acid and/or salts thereof, and the solvent is preferably the same as the one initially used in the reaction system. If the phosphinates are not soluble in the solvent, it may be added continuously in the form of solid.

The additionally added phosphinic acid and/or salts thereof can be added by mixing with the initiator, or they can also be added through respective feed inlets thereof.

The addition of additional phosphinic acid and/or salts thereof can be terminated when the total mole fractions of the monoalkyl phosphinic acids or salts thereof in their declining curves are reduced to 10% or less of the total moles of phosphorus in the reaction system (see FIG. 1). It is preferable that the addition of additional phosphinic acid or salts thereof are terminated when the total mole fractions of the monoalkyl phosphinic acids or salts thereof are reduced to 8% or less, more preferably 5% or less, and particularly preferably 3% or less.

The total mole fractions of the monoalkyl phosphinic acids and/or salts thereof can be easily determined by phosphorus NMR spectrum. Generally speaking, its (their) content is(are) initially gradually increased as the reaction time, and after reaching the maximum value, typically 55-70% of the total moles of phosphorous in the reaction system, it is decreased gradually in one-way. See FIG. 1.

Alternatively, it is preferable that after finishing the addition of all the phosphinic acids and/or salts thereof, continuously adding alkene and initiator until the mole fractions of the monoalkyl phosphinic acids and/or salts thereof account for 1% or less of the total molar contents of phosphorus in the reaction system.

Alternatively, it is preferable that the resulting dialkylphosphinic acids and/or salts thereof are further reacted with compounds of Mg, Ca, Al, Zn, Ti, Sn, Zr and Fe to produce the corresponding metal salts of dialkylphosphinates. If the type of the salt initially selected is the same as the type of the metal salt in the ultimate desired product, this step may be omitted.

The contents of the long chain alkyl phosphinic acids and/or salts thereof and the monoalkyl phosphinic acids and/or salts thereof can be reliably controlled by the method of the present invention, and the reaction time of this method is shorter than the time required in the reaction of reacting the phosphinic acid and/or salts thereof which are added at one time with the alkenes. It is assumed that the reasons are as follows:

The dialkylphosphinic acids/salts thereof is formed in two steps. The first step is to form monoalkyl phosphinic acids/salts thereof, which is a normal reaction. The second step is the addition of the monoalkyl phosphinic acids/salts thereof to the alkenes initiated by the action of free radicals to form radical intermediate I which is a nucleophilic free radical. To achieve the chain reaction, it must capture H in the P—H bond of the monoalkyl phosphinic acids/salts thereof. However, due to the electron donating effect of alkyl groups, the electrophilicity of the monoalkyl phosphinic acids/salts thereof P is reduced, therefore the reaction C becomes difficult, which slows down the conversion of the monoalkyl phosphinic acids/salts thereof, and provides an opportunity for the reaction D to produce long chain alkyl phosphinic acids/salts thereof. In the presence of phosphinic acid/salts thereof, this situation is changed. The phosphinic acid/salts thereof are good hydrogen donors, and the radical intermediate I can easily capture hydrogen atoms from the phosphinic acid/salts thereof to produce dialkylphosphinic acids/salts thereof and free radical II. The free radical II transfers free radicals to the monoalkyl phosphinic acids/salts thereof so as to re-initiate the reaction, and re-generate phosphinic acid/salts thereof. During this process, the phosphinic acid/salts thereof are used as free radical transfer agents and catalysts, and the reaction scheme is shown below. The function of the phosphinic acid/salts thereof as free radical transfer agent is very obvious at the later stage of the reaction, especially after more than 95% of the phosphinic acid/salts thereof in the reaction system are consumed. The addition of additional phosphinic acid/salts thereof can not only accelerate the reaction rate, but also reliably control the contents of the long chain alkyl phosphinic acids/salts thereof and the monoalkyl phosphinic acids/salts thereof.

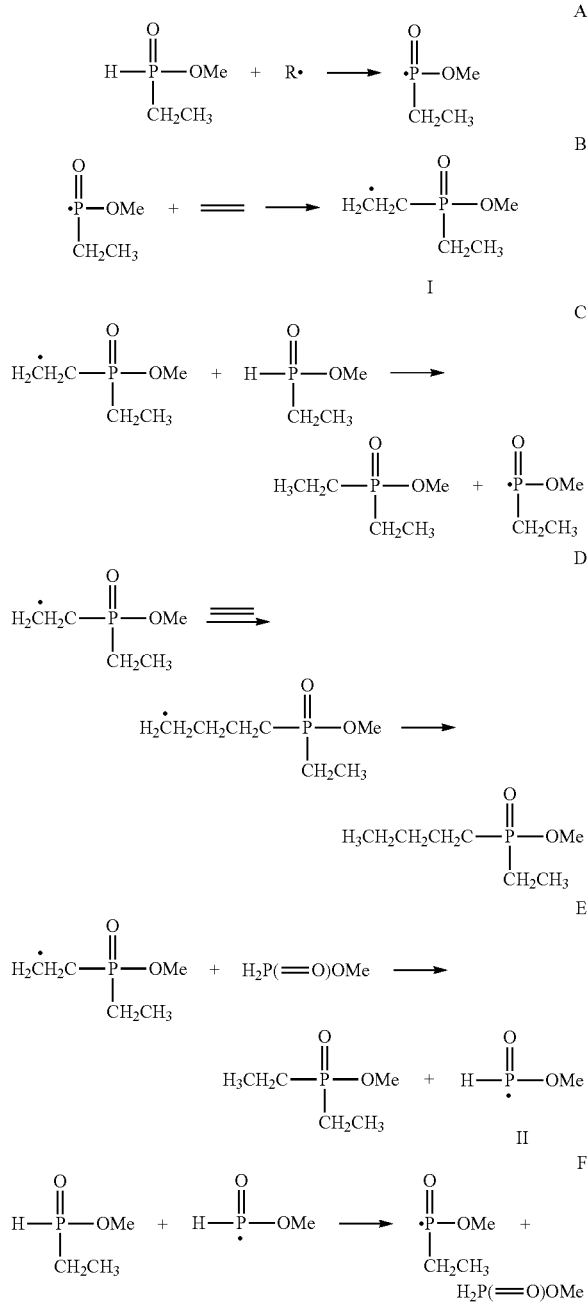

According to the method of additionally adding phosphinic acid and/or salts thereof disclosed in the present invention, the solubility of the alkenes in the reaction mediums is also increased. Due to the salting-out effect of the phosphinic acid and/or salts thereof acting on the alkenes, if the phosphinic acid and/or salts thereof are added at one time, the solubility of the alkenes in the solvent is reduced. If the phosphinic acid and/or salts thereof are added dropwise during the reaction, the solubility of the alkenes in the reaction mediums is relatively high at the beginning, thereby the reaction can be accelerated so as to shorten the reaction time.

After the addition of additional phosphinic acid and/or salts thereof is completed, the reaction enters into an incubation period until the reaction is terminated. The initiator may also be added continuously and the reaction proceeds in the presence of the alkenes, until the contents of the monoalkyl phosphinic acids and/or salts thereof meet the requirements.

The solvents in the resulting reaction mixtures are removed and water is added, then the pH is adjusted to a suitable range, under which the desired metal salts of dialkylphosphinates can be precipitated out. Then a metal compound is added to produce the corresponding dialkylphosphinate precipitates. If the initially used salt ion is identical to that in the desired products, the dialkylphosphinate products can be obtained directly in this step after adjusting the pH value.

According to a preferred embodiment of the present invention, in the presence of organic acid solvents, water or their mixtures, 0-99% of the total amount of phosphinic acid and/or salts thereof are firstly added into a reaction kettle, then the remaining phosphinic acid and/or salts thereof and an initiator together with the alkenes are continuously added into the reaction kettle, and the reaction temperature is controlled at 60-140° C., when the total mole fractions of the monoalkyl phosphinic acids and/or salts thereof account for 10% or less of the total moles of phosphorus in the reaction system, the addition of phosphinic acid and/or salts thereof is stopped, but the initiators and alkenes are continuously added until the total mole fractions of the monoalkyl phosphinic acid and/or salts thereof account for 1% or less of the total moles of phosphorus in the reaction system. The organic solvents are removed, and water is added, the pH is adjusted to a range required for the precipitation of the dialkylphosphinates. A water-soluble salt of Mg, Ca, Ba, Fe, Zr, Sn, Sr, Sb, Ge, Ti and Zn, etc. is added to obtain a dialkylphosphinate precipitate, which is then filtered, washed with water, and dried.

According to the second preferred embodiment of the present invention, water is used as a solvent, 0-99% of the total weight of aluminum phosphinate is firstly added into the reaction kettle, and then 1-100% of the total weight of aluminum phosphinate and an initiator together with alkene are added into the reaction kettle, and the reaction temperature is controlled at 60-140° C., when the mole fraction of aluminum monoalkyl phosphinate accounts for 10% or less of the total mole contents of phosphorus in the reaction system, the addition of aluminum phosphinate is stopped, but the initiator and alkene are continuously added until the mole fraction of aluminum monoalkyl phosphinate accounts for 1% or less of the total mole moles of phosphorus in the reaction system. The aluminum dialkylphosphinate obtained is filtered, washed with water, and dried.

The present invention also particularly relates to a method for preparing aluminum diethylphosphinate. The preparation method comprises the following steps: in the presence of ethylene, peroxide initiator and acetic acid, at least 1% of the total weight of sodium phosphinate is continuously added into the reaction system during the reaction process, until the mole fraction of sodium monoethyl phosphinate is reduced to 10% or less. Then, the reaction proceeds in the presence of ethylene and peroxide, until the mole fraction of sodium monoethyl phosphinate accounts for 1% or less of the total moles of phosphorus in the reaction system. Acetic acid is removed in vacuo, water is added, and the pH is adjusted to 3, then the obtained mixture is mixed with aqueous solution of aluminum sulfate to form aluminum diethylphosphinate.

The present invention also provides a diethylphosphinate flame retardant. The diethylphosphinate flame retardant is prepared by the above various methods. The flame retardant can be used in a variety of polymer materials which for example can be one or more of polyamide, polyester, nylon 6, nylon 6/6, polyalkene and epoxy resins.

The Beneficial Effects of the Invention

Compared with the prior art, the beneficial effects of the present invention are embodied in:
According to the present invention, at least 1% of the phosphinic acid and/or salts thereof are added during the reaction of the phosphinic acid and/or salts thereof with the alkenes. Preparing dialkylphosphinic acids and/or salts thereof prepared by the method can not only very reliably control the contents of the long chain alkyl phosphinic acids and/or salts thereof and the monoalkyl phosphinic acids and/or salts thereof, but also reduce the reaction time to be shorter than the method in which adding the phosphinic acids and/or salts thereof at one time. Furthermore, this method has the advantages of high total yield and high purity of the products.

BRIEF DESCRIPTION OF THE FIGURE

FIG. 1 shows the change of the contents of the monoalkyl phosphinic acids/salts thereof over the reaction time, in which the ordinate is molar percentage content; and the abscissa is reaction time (hour).

EMBODIMENTS OF THE INVENTION

Example 1

1009 g (9.52 mol) of sodium phosphinate monohydrate, 3333 g of acetic acid and 15 g of activated carbon were added into 10 L enamel reaction kettle, which was then sealed and purged with nitrogen twice under stirring. Ethylene was passed through a pressure reducer set to 0.3 MPa and then was fed into the kettle, until the pressure displayed by the pressure gauge of the kettle was 0.3 MPa. The heating device was turned on, and when the reaction mixture was heated to 100° C., ethylene was continuously added into the kettle until the pressure reached 0.5 MPa. 505 g (4.76 mol) of sodium phosphinate monohydrate and 50.1 g (0.258 mol) of t-butyl peroxybenzoate in 2592 g of acetic acid solution was added into the kettle at a constant speed within 13 h through a metering pump, and then incubated for 15 minutes to obtain a mixed solution of diethyl phosphinate sodium-acetic acid.

31P-NMR analysis (mol %):
Sodium diethylphosphinate: 84.9%
Sodium ethylbutylphosphinate: 4.7%
Sodium ethylphosphinate: 7.2%
Sodium ethylphosphonate: 1.1%
Sodium phosphinate: 1.3%
Others: 0.8%

Example 2

1262 g (11.906 mol) of sodium phosphinate monohydrate, 5 kg of acetic acid were added into 10 L enamel reaction kettle, which was then sealed and purged with nitrogen twice under stirring. Ethylene was passed through a pressure reducer set to 0.3 MPa and then was fed into the kettle, until the pressure displayed by the pressure gauge of the kettle was 0.3 MPa. The heating device was turned on, and when the reaction mixture was heated to 100° C., ethylene was continuously added into the kettle until the pressure reached 0.5 MPa. 227.84 g (2.15 mol) of sodium phosphinate monohydrate and 62.02 g (0.319 mol) of t-butyl peroxybenzoate in 1101 g of acetic acid solution was added into the kettle at a constant speed within 15 h through a metering pump. The reaction temperature was raised to 110° C., and 5.07 g (0.026 mol) of t-butyl peroxybenzoate in 111.7 g of acetic acid solution was continuously added into the kettle through the metering pump within 2 h, and then incubated for 15 minutes. After cooled and vented, 8478 g of a mixed solution of sodium diethyl phosphinate-acetic acid was obtained, wherein the absorption amount of ethylene was 804 g (102% of the theoretical value).

31P-NMR Analysis:

TABLE 1

| | time (hour) | | |
| --- | --- | --- | --- |
| | 6 | 12.5 | 17 |
| Sodium diethylphosphinate | 29.9% | 85.5% | 90.9% |
| Sodium ethylbutylphosphinate | 0.3% | 4.1% | 6.9% |
| Sodium ethylphosphinate | 57.1% | 8.3% | 0.5% |
| Sodium ethylphosphonate | 0 | 0.9% | 1.3% |
| sodium phosphinate | 11.9% | 0.4 | 0 |
| others | 0.8% | 0.8% | 0.4% |

Example 3

1000 g (9.434 mol) of sodium phosphinate monohydrate, 5 kg of acetic acid were added into 10 L enamel reaction kettle, which was then sealed and purged with nitrogen twice under stirring. Ethylene was passed through a pressure reducer set to 0.3 MPa and then was fed into the kettle, until the pressure displayed by the pressure gauge of the kettle was 0.3 MPa. The heating device was turned on, and when the reaction mixture was heated to 100° C., ethylene was continuously added into the kettle until the pressure reached 0.5 MPa. 396.6 g (3.742 mol) of sodium phosphinate monohydrate and 42.93 g (0.221 mol) of t-butyl peroxybenzoate in 1322 g acetic acid solution was added into the kettle at a constant speed within 11 h and 40 mins through a metering pump. The reaction temperature was raised to 110° C., and 9.35 g (0.048 mol) of t-butyl peroxybenzoate in 178 g of acetic acid solution was continuously added into the kettle through the metering pump in 2.5 h. The kettle was cooled to room temperature and was depressurized, and 8520 g of a mixed solution of sodium diethyl phosphinate-acetic acid was obtained.

31P-NMR analysis:
Sodium diethylphosphinate: 90.08%
Sodium ethylbutylphosphinate: 8.01%
Sodium ethylphosphinate: 0.45%
Sodium ethylphosphonate: 1.1%
Sodium phosphinate: 0%
Others: 0.36%

The absorption amount of ethylene was 758.8 g (103% of the theoretical value).

Similar results can be obtained by using phosphinate selected from the phosphinic acid salts of Li, K, Mg, Ca, Ba, Fe, Zr, Al, Sn, Sr, Sb, Ge, Ti and Zn, to respectively replace the sodium salt in Example 3 and carry out the reaction described in Example 3, and in the final mixed solution of sodium diethyl phosphinate-acetic acid, the mole percentage contents of the ethyl phosphinate was less than 0.5% and the mole percentage contents of the ethyl butyl phosphinate was less than 10%.

Azobis(isobutyronitrile), 4,4'-azobis (4-cyano pentanoic acid), 2,2'-azobis (2-methyl butyronitrile), 2,2'-azobis (2-amidino propane) dihydrochloride, 2,2'-azodiisobutyl amidinedihydrochloride, hydrogen peroxide, ammonium persulfate, potassium persulfate, sodium persulfate, sodium percarbonate, benzoyl peroxide, di-t-butyl peroxide and peracetic acid were used to respectively replace t-butyl peroxybenzoate and carry out the reaction described in Example 3, the experiments demenstrated that the type of the initiators has little effect on product quality, and the reaction time was 15 hours or less.

Example 4

1) Preparation of Sodium Diethylphosphinate 1000 g (9.434 mol) of sodium phosphinate monohydrate, 5 kg of acetic acid and 5 g of activated carbon were added into 10 L enamel reaction kettle, which was then sealed and purged with nitrogen twice under stirring. Ethylene was passed through a pressure reducer set to 0.3 MPa and then was fed into the kettle, until the pressure displayed by the pressure gauge of the kettle was 0.3 MPa. The heating device was turned on, and when the reaction mixture was heated to 100° C., ethylene was continuously added into the kettle until the pressure reached 0.5 MPa. 366.9 g (3.461 mol) of the sodium phosphinate monohydrate and 38.76 g (0.2 mol) of the t-butyl peroxybenzoate in 1223 g acetic acid solution were added into the kettle at a constant speed within 11 h and 40 mins through a metering pump. At this time, the concentration of the sodium ethyl phosphinate was less than 10% calculated according to the absorption weight of the ethylene. The reaction temperature was raised to 110° C., and 5.49 g (0.028 mol) of t-butyl peroxybenzoate in 177 g of acetic acid solution was continuously added into the kettle through the metering pump within 2.5 h. The kettle was cooled to room temperature and was depressurized, and 8567 g of a mixed solution of sodium diethyl phosphinate-acetic acid was obtained.

31P-NMR analysis:
Sodium diethylphosphinate: 89.02%
Sodium ethylbutylphosphinate: 8.82%
Sodium ethylphosphinate: 0.57%
Sodium ethylphosphonate: 1.21%
sodium phosphinate: 0%
others: 0.38%

The absorption amount of ethylene was 744.8 g (103% of the theoretical value).

2) Preparation of Aluminum Diethylphosphinate 33.3 g of the above solution was weighted, and acetic acid was removed in vacuo, then the solution was formulated into a 10% aqueous solution with the pH adjusted to 3, and the solution was added dropwise slowly into a 6% aqueous solution of aluminum sulfate, reacting under stirring for 0.5 h to produce a white solid, which was filtered and the precipitate was washed with 600 ml water, dried at 130° C. for 10 h to obtain the aluminum diethylphosphinate with a yield of 86.6%.

In step 2), if desired, water-soluble salts of Mg, Ca, Ba, Fe, Zr, Sn, Sr, Sb, Ge, Ti, Zn and the likes were selected for replacement so as to obtain the desired diethylphosphinate.

Application Example 1

Nylon 66 (containing 35% glass fiber) was dried in a vacuum oven at 110° C. for 4 hours. Thereafter, 70 parts (Unless otherwise specified, all parts were by weight) was mixed with 30 parts of aluminum diethylphosphinate prepared according to the method of Example 4, and the mixture was internally mixed for 3 minutes at 270° C. in a Brabender torque rheometer. After dried, it was processed by a plate vulcameter at 290° C. to obtain a flame retardant polymer molded product, which was cut into specimens with a size of 100 mm×13 mm×3.2 mm by a universal specimen-making machine. A test was carried out according to GB/T 2408-2008 standard by using AG5100B horizontal-vertical burning tester, the results demenstrated that a UL94 V-0 flame rating can be reached.

Comparative Example 1

Referring to Example 2, except that all the sodium phosphinates were added into the kettle at one time before the reaction begins and only the initiator and ethylene were added during the reaction, other procedures were the same as Example 2. The reaction progress was tracked through the absorbtion amount of ethylene and checked by NMR. After 32 hours, the reaction was terminated.

31P-NMR analysis:

TABLE 2

|  | time (hour) | | | |
| --- | --- | --- | --- | --- |
|  | 11 | 17 | 28 | 32 |
| Sodium diethylphosphinate | 16.4% | 46.0% | 86.7% | 89.9% |
| Sodium ethylbutylphosphinate | 0 | 0.7% | 5.8% | 7.6% |
| Sodium ethylphosphinate | 63.8% | 50.4% | 6.0% | 1.2% |
| Sodium ethylphosphonate | — | — | 0.9% | 0.9% |
| sodium phosphinate | 18.9% | 2.4% | 0 | 0 |
| others | 0.9% | 0.4% | 0.6% | 0.4% |

It can be seen that, comparing with the sodium phosphinate was added at one time at the beginning of the reaction, the reaction time required is substantially reduced by continuously adding 1-100% of the total amount of the sodium phosphinate into the reaction solution during the reaction process, and the content of the sodium monoalkyl phosphinate is much lower.

What is claimed is:

1. A process for preparing dialkylphosphinate, comprising the following steps:
   (1) firstly adding 0-99% of a total weight of phosphinic acid and/or salts thereof, and a solvent into a reaction kettle;
   (2) in the reaction kettle also including an alkene and an initiator, continuously adding 1-100% of the total weight of phosphinic acid and/or salts thereof into the reaction kettle, and when a total mole fraction of monoalkyl phosphinic acids and/or salts thereof in their declining curves account for 10% or less of a total of moles of phosphorus in the reaction kettle, stopping adding additional phosphinic acid and/or salts thereof, thereby obtaining dialkylphosphinic acids and/or salts thereof.

2. The process for preparing dialkylphosphinate according to claim 1, characterized in that, the phosphinic acid and/or salts thereof is one or more of the phosphinic acid and/or salts thereof of Li, Na, K, Mg, Ca, Ba, Fe, Zr, Al, Sn, Sr, Sb, Ge, Ti and Zn.

3. The process for preparing dialkylphosphinate according to claim 1, characterized in that, the initiator is one or more of azo initiators, peroxide initiators and photoinitiators.

4. The process for preparing dialkylphosphinate according to claim 3, characterized in that, an amount of moles of the initiator added is 0.1-5% of a total of moles of the phosphinic acid and/or salts thereof.

5. The process for preparing dialkylphosphinate according to claim 4, characterized in that, the initiator is one or more of azobis(isobutyronitrile), 4,4'-azobis(4-cyano pentanoic acid), 2,2'-azobis(2-methyl butyronitrile), 2,2'-azobis(2-amidino propane) dihydrochloride and 2,2'-azodiisobutyl amidinedihydrochloride.

6. The process for preparing dialkylphosphinate according to claim 4, characterized in that, the initiator is one or more of hydrogen peroxide, ammonium persulfate, potassium persulfate, sodium persulfate, sodium percarbonate, benzoyl peroxide, di-tert-butyl peroxide, t-butyl perbenzoate and peracetic acid.

7. The process for preparing dialkylphosphinate according to claim 1, characterized in that, the alkene has the following structure:

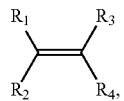

wherein R1-R4 are each independently of hydrogen, C1-18 alkyl or cycloalkyl, phenyl, benzyl, alkyl-substituted phenyl group or alkoxy ketone group.

8. The process for preparing dialkylphosphinate according to claim 1, characterized in that, the solvent is an organic carboxylic acid, water or their mixture.

9. The process for preparing dialkylphosphinate according to claim 1, having a reaction temperature of 20-180° C.

10. The process for preparing dialkylphosphinate according to claim 1, having a reaction pressure of 0.1-5 MPa.

11. The process for preparing dialkylphosphinate according to claim 1, characterized in that, activated carbon or charcoal is simultaneously added into the reaction kettle when adding the phosphinic acids and/or salts thereof.

12. The process for preparing dialkylphosphinate according to claim 11, characterized in that, a weight of the charcoal or the activated carbon used is 0.01%-5% of a total weight of a solution.

13. The process for preparing dialkylphosphinate according to claim 1, characterized in that, the phosphinic acid and/or salts thereof are added in such a manner: firstly 1-99% of the total weight of the phosphinic acid and/or salts thereof is added in step (1), and 1-99% of the total weight of the phosphinic acid and/or salts thereof is added in step (2).

14. The process for preparing dialkylphosphinate according to claim 13, characterized in that, the phosphinic acid and/or salts thereof are added in such a manner: firstly 60-85% of the total weight of the phosphinic acid and/or salts thereof is added in step (1), then 15-40% of the total weight of the phosphinic acid and/or salts thereof is added in step (2).

15. The process for preparing dialkylphosphinate according to claim 1, characterized in that, in step (2), the added phosphinic acid and/or salts thereof is added in the form of solid or solution, and when added as solution, a solvent used is the same as the solvent used in the reaction kettle.

16. The process for preparing dialkylphosphinate according to claim 1, characterized in that, in step (2), after finishing the addition of phosphinic acid and/or salts thereof, continuously adding alkenes and initiators until the total mole fraction of monoalkyl phosphinic acids and/or salts thereof account for 1% or less of the total moles of phosphorus in the reaction kettle.

17. The process for preparing dialkylphosphinate according to claim 1, characterized in that, in step (1), when the phosphinic acid and/or salts thereof added are not the phosphinic acid and/or salts thereof salts of Mg, Ca, Al, Zn, Ti, Sn, Zr and Fe, the produced dialkylphosphinic acids and/or salts thereof are further reacted with compounds of Mg, Ca, Al, Zn, Ti, Say, Zr and Fe in step (2), thereby producing a corresponding metal salts of dialkylphosphinates.

18. The process for preparing dialkylphosphinate according to claim 1, characterized in that, the phosphinic acid and/or salts thereof is aluminum phosphinate, and a reaction temperature is 60-140° C.

19. The process for preparing dialkylphosphinate according to claim 18, characterized in that, the alkene is ethylene; and during a reaction, aluminum phosphinate accounting for at least 1% of the total weight of the phosphinic acid and/or salts thereof is continuously added into the reaction system until a mole fraction of the aluminum monoethylphosphinate is reduced to 10% or less in its declining curve.

* * * * *

UNITED STATES PATENT AND TRADEMARK OFFICE
CERTIFICATE OF CORRECTION

PATENT NO. : 9,802,970 B2  
APPLICATION NO. : 15/122345  
DATED : October 31, 2017  
INVENTOR(S) : Qiang Yao et al.

Page 1 of 1

It is certified that error appears in the above-identified patent and that said Letters Patent is hereby corrected as shown below:

In the Claims

At Column 12, Claim number 17, Line number 36, the word "Say" should read -- Sn --.

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*